United States Patent
Zukowski

(10) Patent No.: US 9,402,751 B2
(45) Date of Patent: Aug. 2, 2016

(54) DEVICES AND METHODS FOR TREATMENT OF THE AORTIC ARCH

(71) Applicant: W. L. Gore & Associates, Inc., Newark, DE (US)

(72) Inventor: Stanislaw L. Zukowski, Flagstaff, AZ (US)

(73) Assignee: W. L. GORE & ASSOCIATES, INC., Newark, DE (US)

( * ) Notice: Subject to any disclaimer, the term of this patent is extended or adjusted under 35 U.S.C. 154(b) by 5 days.

(21) Appl. No.: 14/189,814

(22) Filed: Feb. 25, 2014

(65) Prior Publication Data

US 2014/0316514 A1    Oct. 23, 2014

Related U.S. Application Data

(60) Provisional application No. 61/779,043, filed on Mar. 13, 2013.

(51) Int. Cl.
*A61F 2/07* (2013.01)
*A61F 2/856* (2013.01)
*A61F 2/06* (2013.01)

(52) U.S. Cl.
CPC . *A61F 2/856* (2013.01); *A61F 2/07* (2013.01); *A61F 2002/061* (2013.01); *A61F 2250/006* (2013.01); *A61F 2250/0039* (2013.01); *A61F 2250/0065* (2013.01)

(58) Field of Classification Search
CPC .................................... A61F 2/07; A61F 2/06
USPC ................................................ 623/1.31–1.35
See application file for complete search history.

(56) References Cited

U.S. PATENT DOCUMENTS

| | | | |
|---|---|---|---|
| 6,908,477 B2 | 6/2005 | McGuckin, Jr. et al. | |
| 7,144,421 B2 | 12/2006 | Carpenter et al. | |
| 7,575,590 B2 | 8/2009 | Watson | |
| 8,167,926 B2 | 5/2012 | Hartley et al. | |
| 2005/0010277 A1 | 1/2005 | Chuter | |
| 2005/0102018 A1* | 5/2005 | Carpenter et al. | 623/1.11 |
| 2007/0168013 A1* | 7/2007 | Douglas | 623/1.12 |
| 2007/0203572 A1* | 8/2007 | Heuser et al. | 623/1.35 |
| 2007/0208410 A1 | 9/2007 | Berra et al. | |
| 2008/0312732 A1* | 12/2008 | Hartley et al. | 623/1.13 |
| 2009/0012596 A1* | 1/2009 | Kocur et al. | 623/1.11 |

(Continued)

FOREIGN PATENT DOCUMENTS

WO    2011/064782    6/2011

OTHER PUBLICATIONS

International Search Report and Written Opinion for PCT/US2014/019296 mailed Jun. 26, 2014, corresponding to U.S. Appl. No. 14/189,814, 5 pages.

*Primary Examiner* — Suzette J Gherbi

(57) ABSTRACT

The present disclosure includes an endoprosthesis comprising a descending stent-graft, an ascending stent-graft, and/or a side-branch stent-graft. In various embodiments, an ascending stent-graft is capable of being coupled to a descending stent-graft, and/or a descending stent-graft can comprise a fenestration capable of being coupled to a side-branch stent-graft. In addition, in various embodiments, a descending and/or ascending stent-graft can comprise a reduced diameter portion that, when implanted within an aortic arch, recedes from a luminal surface of the aortic arch to allow a side-branch stent-graft to be maneuvered within the aortic arch.

29 Claims, 17 Drawing Sheets

(56) References Cited

U.S. PATENT DOCUMENTS

| | | |
|---|---|---|
| 2009/0048663 A1 | 2/2009 | Greenberg |
| 2009/0248135 A1 | 10/2009 | Bruszewski et al. |
| 2009/0281616 A1 | 11/2009 | Iannelli |
| 2010/0057186 A1 | 3/2010 | West et al. |
| 2010/0063576 A1* | 3/2010 | Schaeffer et al. ............ 623/1.13 |
| 2011/0257731 A1 | 10/2011 | Hartley et al. |
| 2012/0130478 A1 | 5/2012 | Shaw |
| 2012/0215300 A1* | 8/2012 | Richardson et al. ......... 623/1.36 |

* cited by examiner

DEVICES AND METHODS FOR TREATMENT OF THE AORTIC ARCH

BACKGROUND

1. Field

The present disclosure generally relates to endoprostheses for treating diseases of the vasculature, and more particularly to endoprostheses comprising a plurality of stent-grafts for treating an aortic arch.

2. Discussion of the Related Art

Stent-grafts are endoprosthetic medical devices (or endoprostheses) constructed to reinforce, replace, bridge, or otherwise treat a part of a blood vessel. A stent-graft may thus guide blood flow through a lumen defined by a generally tubular interior of such a vessel.

Occasionally, it may be necessary to implant a stent-graft within a main vessel of a patient's body such that the stent-graft would, without adaptation, occlude or block one or more side-branch vessels extending from the main vessel. Thus, to permit blood to flow between a main vessel and a side branch vessel, certain fenestrated stent-grafts have been developed. Stent-grafts of this type can be coupled to one or more side branch stent-grafts, so that blood is allowed to flow between a main vessel and a side branch vessel.

It has been important, however, with prior art fenestrated stent-grafts to ensure proper alignment between fenestration and side-branch artery, as for example, improper alignment may reduce or halt blood flow between a main vessel and a side-branch vessel.

In light of these shortcomings, an improved fenestrated stent-graft and a method for deploying the same are desirable. More particularly, an improved fenestrated stent-graft for repair of the aortic arch, as disclosed herein, is desirable.

BRIEF DESCRIPTION OF THE DRAWINGS

The features and advantages of the present disclosure will become more apparent from the detailed description set forth below when taken in conjunction with the drawings, wherein.

DETAILED DESCRIPTION OF THE ILLUSTRATED EMBODIMENTS

Figure 1:
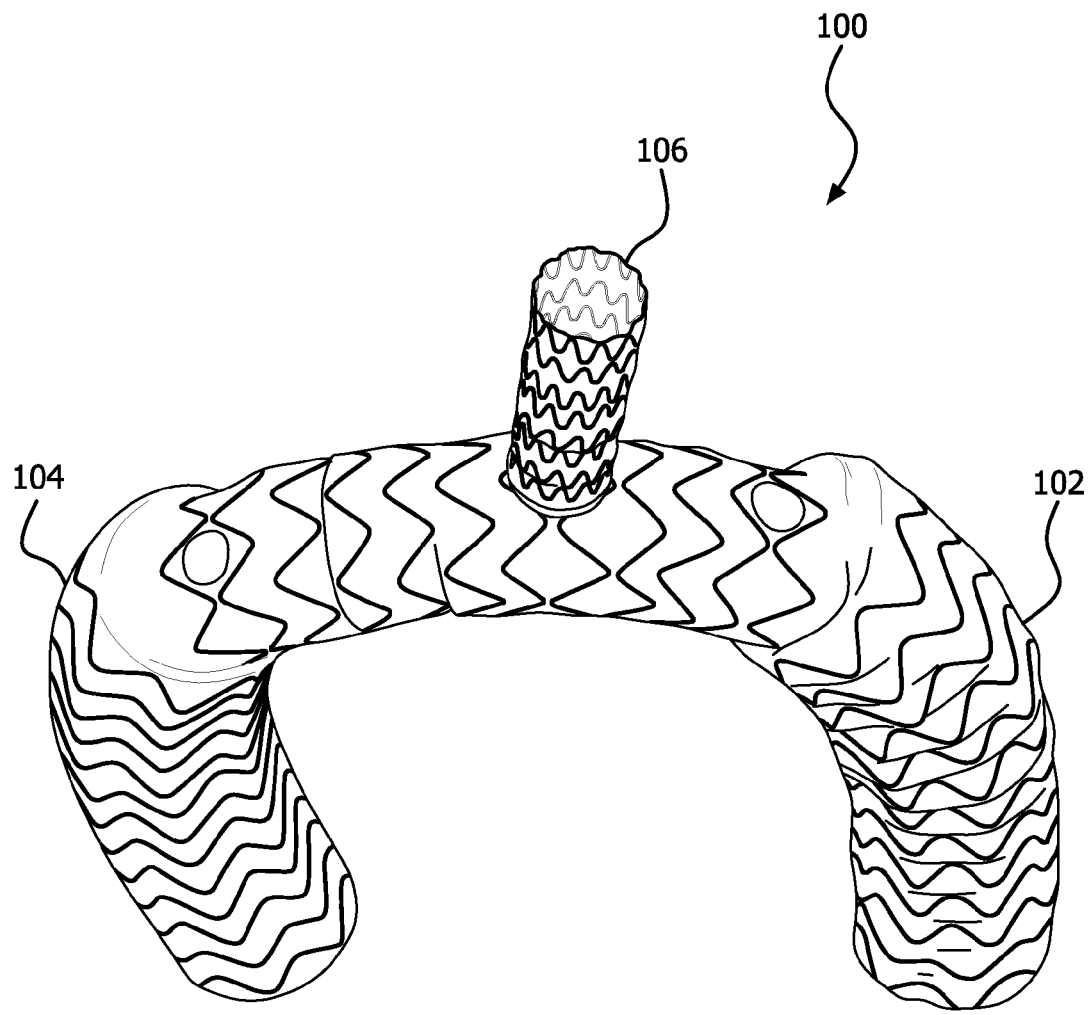
FIG. 1 illustrates an endoprosthetic device.

Persons skilled in the art will readily appreciate that various aspects of the present disclosure may be realized by any number of methods and apparatuses configured to perform the intended functions. Stated differently, other methods and apparatuses may be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

The terms "branch vessel," "side-branch" and/or "side-branch vessel" may refer to a vessel that branches off from a main vessel. For example, "branch vessels" of the aortic arch include, for instance, the innominate artery, the left common carotid artery, and the left subclavian artery. Similarly, branch vessels of the innominate artery include, for example, the right subclavian artery the right carotid artery. Thus, it should be seen that "branch vessel" and "main vessel" are relative terms.

As used herein, the term "constrain" may mean (i) to limit expansion, occurring either through self-expansion or expansion assisted by a device, of the diameter of an expandable implant, or (ii) to cover or surround, but not otherwise restrain, an expandable implant (e.g., for storage or biocompatibility reasons and/or to provide protection to the expandable implant and/or the vasculature).

Throughout this specification and in the claims, the term "distal" refers to a location that is, or a portion of an intraluminal device (such as a catheter, delivery device, and/or endoprosthesis) that when implanted is, farther from a physician or clinician. Similarly, the term "distally" refers to a direction away from a physician or clinician.

The term "proximal" refers to a location that is, or a portion of an intraluminal device (such as a catheter, delivery device, and/or an endoprosthesis) that when implanted is, closer to a physician or clinician. Similarly, the term "proximally" refers to a direction towards a physician or clinician.

With further regard to the terms proximal and distal, this disclosure should not be narrowly construed with respect to these terms. Rather, the devices and methods described herein may be altered and/or adjusted relative to the anatomy of a patient.

While the specific embodiments are described in greater detail below, in general, the present disclosure will focus primarily upon devices and methods for treating the ascending aorta, aortic arch, and descending aorta; however, these devices and methods may be applied to other portions of the vasculature, including, for example, any portion where a larger vessel and one or more branch vessels are to be treated.

Thus, various embodiments can comprise an endoprosthetic device configured to be implanted within a main vessel and/or one or more side branch vessels. More particularly, as discussed in greater detail below, various embodiments can comprise an endoprosthetic device configured to be implanted within an aortic arch and its various side branch vessels (e.g., the innominate, the carotid, and the subclavian vessels).

The present disclosure includes an endoprosthesis comprising a descending stent-graft, an ascending stent-graft, and/or a side-branch stent-graft. In various embodiments, an ascending stent-graft is capable of being coupled to a descending stent-graft, and/or a descending stent-graft can comprise a fenestration capable of being coupled to a side-branch stent-graft. In addition, in various embodiments, a descending and/or ascending stent-graft can comprise a tapered and/or smaller diameter portion that, when implanted within an aortic arch, tapers away and/or recedes from a luminal surface of the aortic arch to allow a side-branch stent-graft to be maneuvered within the aortic arch.

The present disclosure further includes a method comprising steps for deploying a descending stent-graft within a descending portion of an aortic arch, deploying an ascending stent-graft within an ascending portion of the aortic arch, and/or deploying a side-branch stent-graft through a fenestration in one of the ascending stent-graft and the descending stent-graft. In various embodiments, the method may further comprise steps for coupling an ascending stent-graft to a descending stent-graft during deployment, and/or maneuvering a side-branch stent within the aortic arch between a fenestration and an ostium of a side-branch artery. The method may also include steps for precannulating a side-branch artery with a guidewire, where the guidewire can abut a luminal surface of the side-branch artery to facilitate the deployment of the descending stent-graft. Further still, the method can include steps for loading an ascending stent-graft on a guidewire such that a trunk portion of the ascending-stent-graft is located distal to a tapered portion of the ascending stent-graft, and/or imaging one of a descending stent-graft, an ascending stent-graft and/or a side-branch stent-graft by way of a radiopaque marker.

Accordingly, an endoprosthetic device, as described herein, can comprise one or more main stent-grafts and/or a plurality of side branch stent-grafts. In various embodiments, a main stent-graft can comprise an ascending stent-graft and/or a descending stent-graft. In various embodiments, an ascending stent-graft can be deployed within an ascending portion of the aortic arch, while a descending stent-graft can be deployed within a descending portion of an aortic arch. Each main stent-graft can comprise a trunk portion having an expanded or deployed diameter that is substantially equal to a diameter of an aortic arch. A main stent-graft may also comprise a tapered and/or reduced diameter portion having a deployed diameter that is less than a diameter of an aortic arch. In various embodiments, a reduced diameter portion can be deployed so that it does not make contact with, and thereby does not abrade, a substantial portion of a luminal (i.e., inner) surface of a vessel wall. In addition a main stent-graft can comprise one or more fenestrations through which one or more of a plurality of side-branch stent-grafts may couple to the stent-graft, and these fenestrations can be made in a reduced diameter portion of the stent-graft. Further, in various embodiments, an ascending stent-graft can be coupled intraluminally to a descending stent-graft to form an endoprosthetic device capable of treating an aortic arch.

Treatment may proceed, for example, as follows. A pair of guidewires (e.g., a main guidewire and a side-branch guidewire) can be inserted, as those of skill will appreciate, through a lumen of a patient (e.g., a femoral artery) and into an aortic arch of the patient. A main guidewire may precannulate an aortic arch, while a side-branch guidewire may precannulate one or a plurality of side-branch vessels.

In various embodiments, a descending stent-graft can be deployed in a constrained diameter over a main guidewire and/or a side-branch guidewire and expanded to a deployed diameter within a descending portion of an aortic arch. Further, in various embodiments, one or more side-branch stent-grafts can be deployed over one or more side-branch guidewires and through an expanded descending stent-graft. For example, a left subclavian side-branch stent-graft and/or a left common carotid side-branch stent-graft can be deployed from within a descending stent-graft.

Further still, an ascending stent-graft can be deployed in a constrained diameter over a main guidewire and/or a side-branch guidewire and expanded to a deployed diameter within an ascending portion of an aortic arch. Similarly, one or more side-branch stent-grafts can be deployed over a main guidewire and/or a side-branch guidewire and through an expanded ascending stent-graft. For example, an innominate side-branch stent-graft can be deployed from within an ascending stent-graft.

In addition, as discussed herein, each side-branch stent-graft can be coupled to a reduced diameter portion of a main stent-graft, so that each of these side-branch stent-grafts only minimally contacts, or does not make contact with a substantial portion of a luminal surface of the aortic arch. In other words, one or more side-branch stent-grafts can find room between an abluminal (i.e., outer) surface of the main-stent-graft to which it is coupled and a luminal surface of the aortic arch. A side-branch stent-graft may extend through or into a side-branch vessel. Thus, the endoprosthetic device and methods discussed herein overcome the deficiencies associated with the prior art, as discussed above. For example, the endoprosthetic device and methods presented here permit the maneuvering of each of a plurality of side-branch stent-grafts within an aortic arch, so that it is not necessary to align a fenestration in a main stent-graft with a side-branch vessel. Rather, each side-branch stent-graft can be deployed out of alignment with its corresponding side-branch vessel, but maneuvered during deployment to treat the desired side branch vessel. In addition, an endoprosthetic device, as discussed herein, can be deployed such that a substantial portion of the endoprosthetic device (e.g., one or more side-branch stent-grafts, or a reduced diameter portion of a main stent-graft) does not abrade or make contact with a substantial portion of a luminal surface of a vessel wall. Thus, the devices and methods disclosed herein can be adapted to the individual anatomies of a variety of non-uniform or individual patients.

With reference now to FIG. 1, an endoprosthetic device 100 is shown. As discussed above, an endoprosthetic device 100 can comprise one or more main stent-grafts and/or one or more side-branch stent-grafts. A main stent-graft can comprise a descending stent-graft 102 and/or an ascending stent-graft 104. Thus, as shown, an endoprosthetic device 100 can comprise a descending stent-graft 102, an ascending stent-graft 104, and/or one or more side-branch stent-grafts 106.

Figure 2:
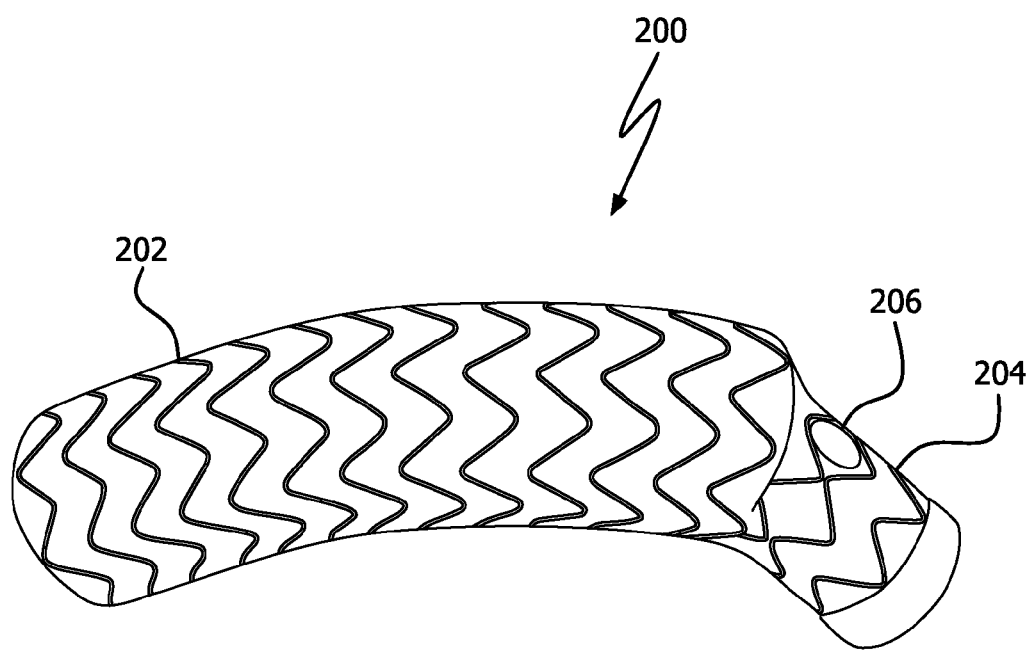
FIG. 2 illustrates a main stent-graft having a single fenestration.

Referring to FIG. 2, a main stent-graft 200 can comprise a trunk portion 202 and/or a reduced diameter portion 204. As discussed more particularly below, a main stent-graft 200 can be further constrained for delivery to an aortic arch and expanded within the arch to a deployed diameter. Thus, a trunk portion 202 of a main stent-graft 200 can comprise a deployed diameter that is substantially equal to a luminal diameter of an aortic arch. A reduced diameter portion 204 of a main stent-graft 200 may, on the other hand, comprise a deployed diameter that is less than a luminal diameter of an aortic arch, so that a side-branch stent-graft can be allowed some room to maneuver within the arch. In addition, due to a reduced diameter portion 204 of a main stent-graft 200, the stent-graft 200 may not come into contact with, and so not abrade or irritate, a luminal vessel wall. This can be so, even as blood is pumped through the stent-graft 200.

Figure 3:
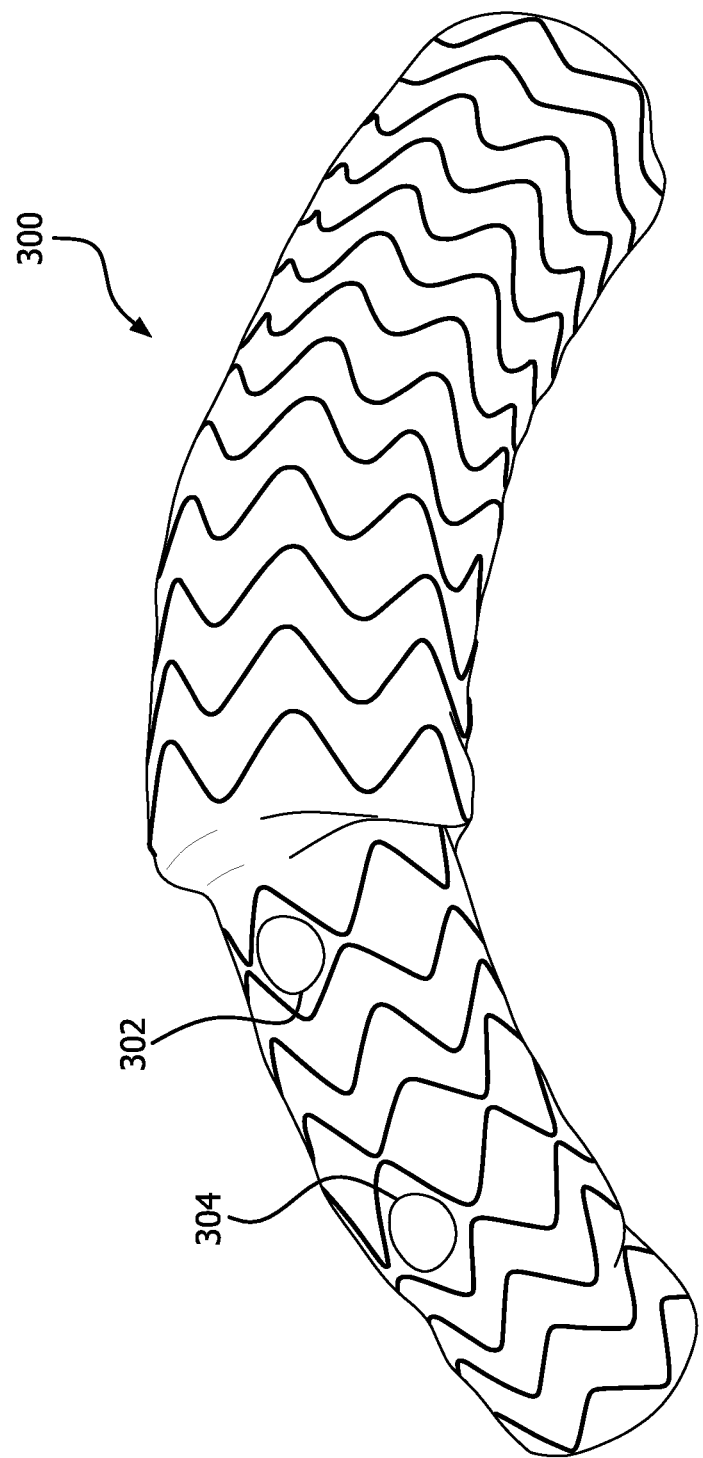
FIG. 3 illustrates a main stent-graft having two fenestrations.

In addition, a main stent-graft 200 can comprise one or more fenestrations 206, each of which may permit the main stent-graft to be coupled to a side-branch stent-graft. For example, in various embodiments, an ascending stent-graft can comprise a single fenestration. Similarly, and with brief reference now to FIG. 3, a descending stent-graft 300 can comprise two fenestrations 302 and 304, each of which may couple to a side-branch stent-graft. In various embodiments, a connection between a fenestration 206 and a side-branch stent-graft can be made between graft material comprising the fenestration 206 or the main stent-graft and graft material comprising the side-branch stent-graft. Thus, a metal-to-metal (e.g., ring-to-ring) connection between a main stent-graft and a side-branch stent-graft can be obviated.

Figure 4:
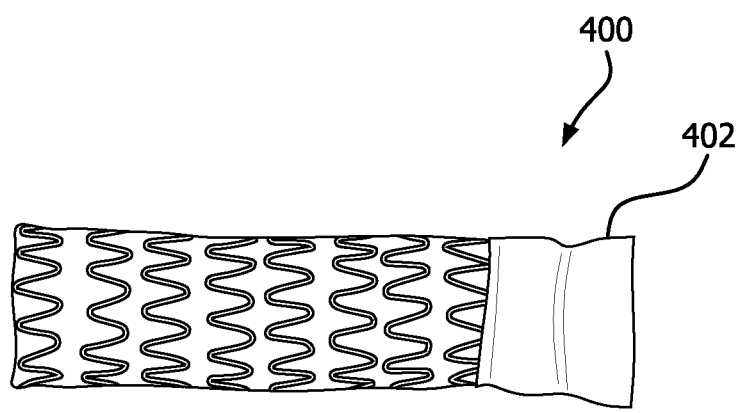
FIG. 4 illustrates a side-branch stent-graft.

Thus, with attention to FIG. 4, a side-branch stent-graft 400 is shown. A side-branch stent-graft 400 can include a cuff 402, which may, in turn, comprise a graft material. In various embodiments, a cuff 402 may span approximately two stent rings in a pre-deployed configuration. Likewise, once coupled to a main stent-graft through a fenestration, a cuff 402 may crumple or fold through frictional contact with the fenestration to span approximately one stent ring. Accordingly, a cuff 402 can form a fluid tight, impermeable, or semi-permeable seal between a side-branch stent-graft 400 and a main stent-graft.

Figure 5:
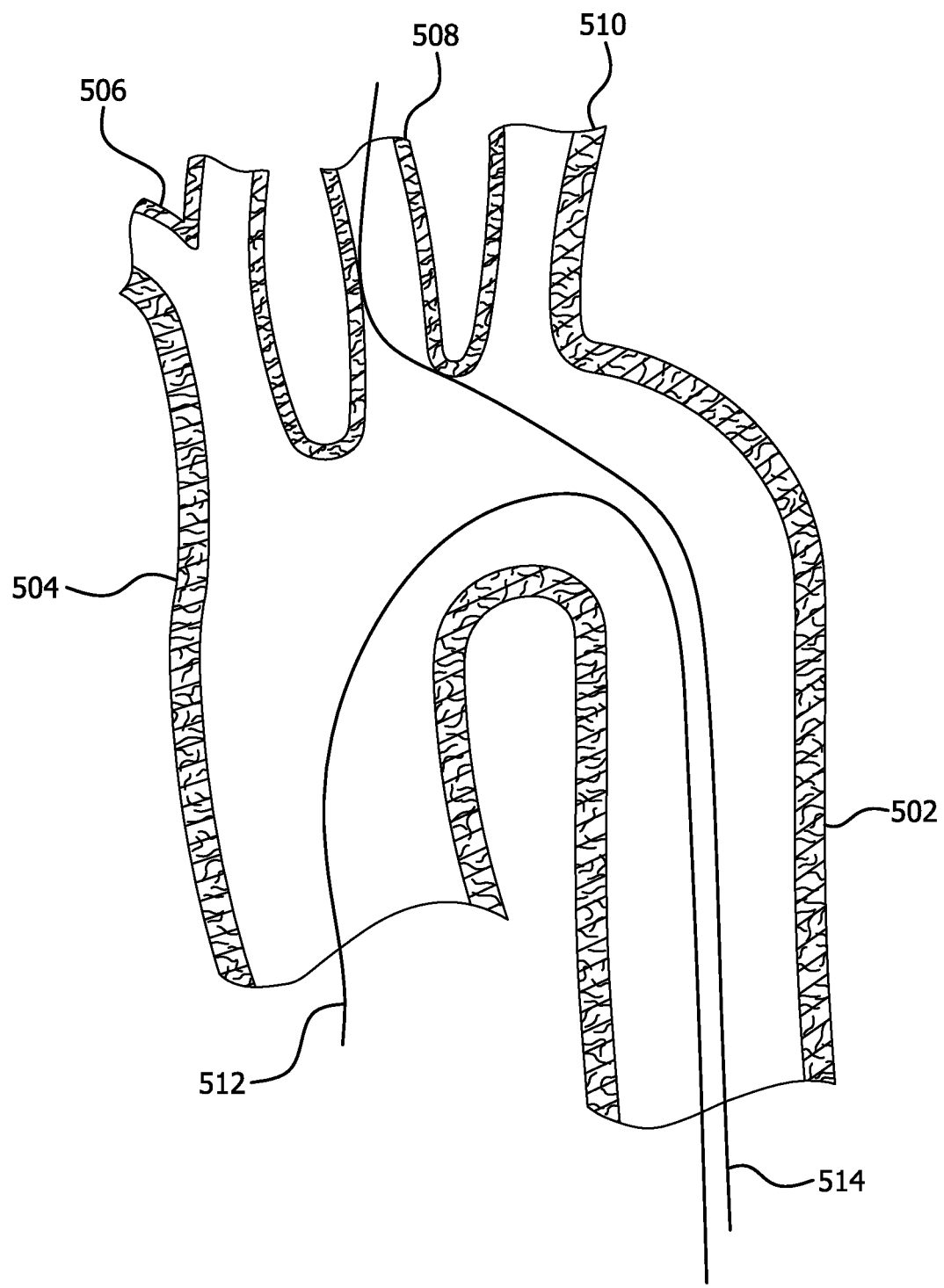
FIG. 5 illustrates cross-sectional view of an aortic arch precannulated by two guidewires.

With reference now to FIG. 5, a cross-sectional view of an aortic arch is depicted. As shown, an aortic arch consists of a descending portion 502, an ascending portion 504, an innominate artery 506, a left common carotid artery 508, and/or a left subclavian artery 510. In operation, a main guidewire 512 and a side-branch guidewire 514 can be inserted within an aortic arch (e.g., as those of skill will appreciate, via a femoral artery of a patient's body). A main guidewire 512 may precannulate the arch itself, while a side-branch guidewire 514 may precannulate one (or more than one, in a sequential fashion) of the side branch vessels (e.g., the innominate, the left common carotid, and/or the left subclavian arteries). Further, in various embodiments, as those of skill will appreciate, a guidewire 512 and/or 514 can comprise a guidewire catheter.

Figure 6:
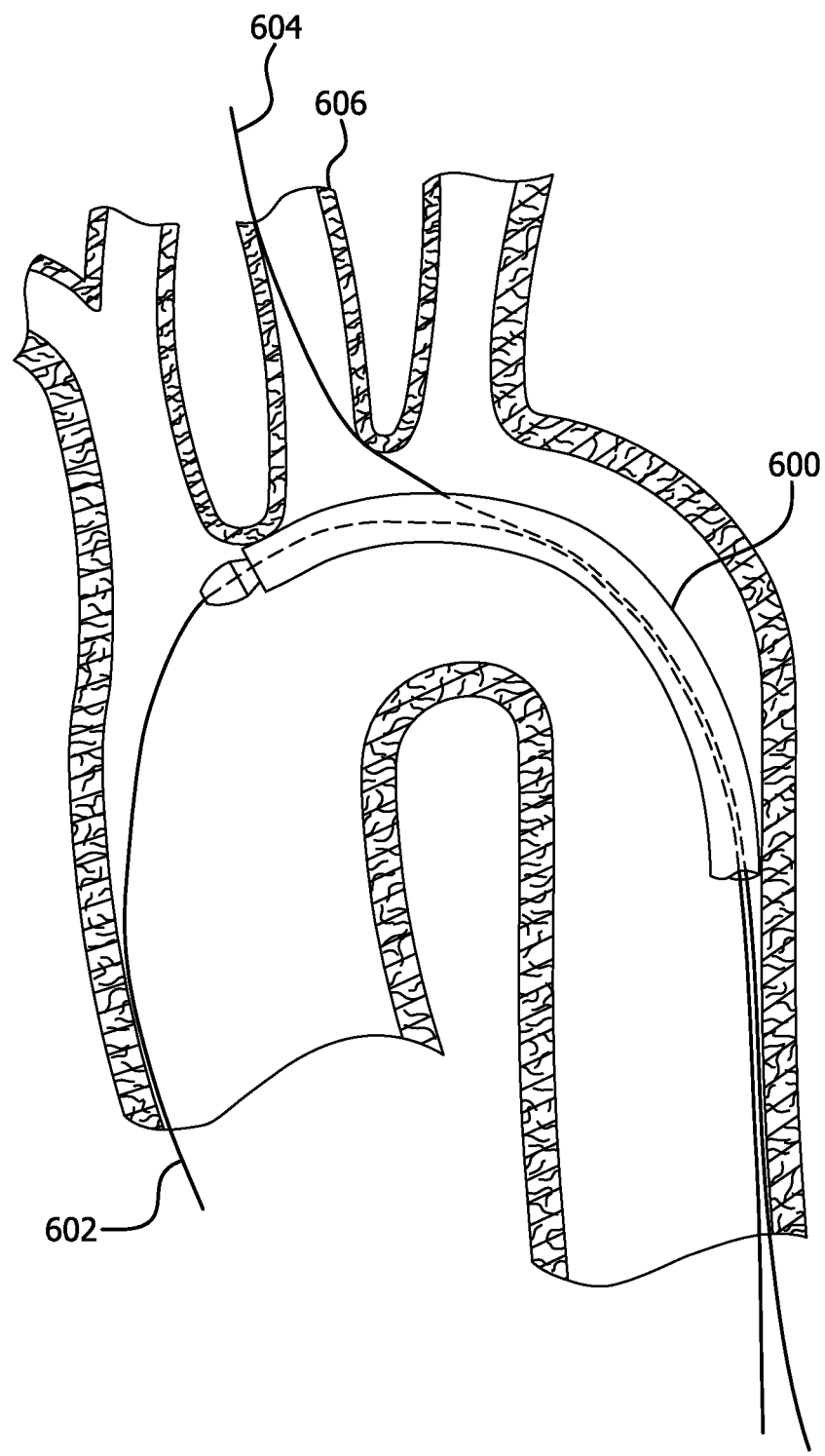
FIG. 6 illustrates a cross-sectional view of an aortic arch receiving a descending stent-graft.

In various embodiments, with reference now to FIG. 6, a catheter can be inserted over a guidewire 602 and/or 604 and loaded with one or more stent-grafts 600 (shown in FIG. 6 as covered with a constraining sleeve). For example, a catheter can be loaded with a descending stent-graft, an ascending stent-graft, and/or one or more side-branch stent-grafts. Moreover, a side-branch guidewire 604 may exit a loaded stent-graft 600 through a fenestration, as discussed herein, in the stent-graft 600.

A stent-graft 600 can be variously deployed from a catheter. For example, a stent-graft 600 can comprise a self-expanding stent-graft, which may expand from a constrained diameter in response to the removal or retraction of a constraining sleeve. A plurality of constraining sleeves can be used, for example, to provide for an intermediate deployed configuration having a diameter that is larger than the delivery diameter, yet smaller that the deployed diameter. A stent-graft 600 can be forced into an expanded configuration by the expansion of a catheter, where for example, the catheter comprises an inflatable balloon catheter. In various embodiments, e.g., where a catheter comprises a guidewire catheter, the same principles may apply, except that a stent-graft 600 can be loaded on a guidewire catheter that is advanced through a body lumen, as opposed to a over a guidewire.

Accordingly, during deployment, a stent-graft 600 may follow the course of a main guidewire 602 and/or one or more side-branch guidewires. More particularly, in various embodiments, a stent-graft 600 may follow the course of a main guidewire 602 and/or a side-branch guidewire 604 until a resistance is encountered. Resistance may arise as a result of contact between a side-branch guidewire 604 and a wall of a fenestration.

For example, as shown, a side-branch guidewire 604 can be advanced through a side-branch artery, such as the left common carotid artery 606, such that the guidewire 604 abuts or makes contact with a luminal wall of the artery 606. As a stent-graft 600 is advanced over each guidewire 602 and 604, the stent-graft 600 may at a point substantially suitable to deployment of the stent-graft 600, encounter some resistance due to the deployment of the side-branch guidewire 604 into a side-branch vessel and resulting contact between a side-branch guidewire 604 and a wall of a fenestration. As discussed further below, this feature may aid in the proper deployment of a stent-graft 600, as the stent-graft 600 can be deployed substantially proximate to one or more side-branch arteries. In various embodiments, a stent-graft 600 may further comprise one or more radiopaque and/or echogenic markers, and these may assist as well in the proper deployment of the stent-graft 600.

Figure 7:
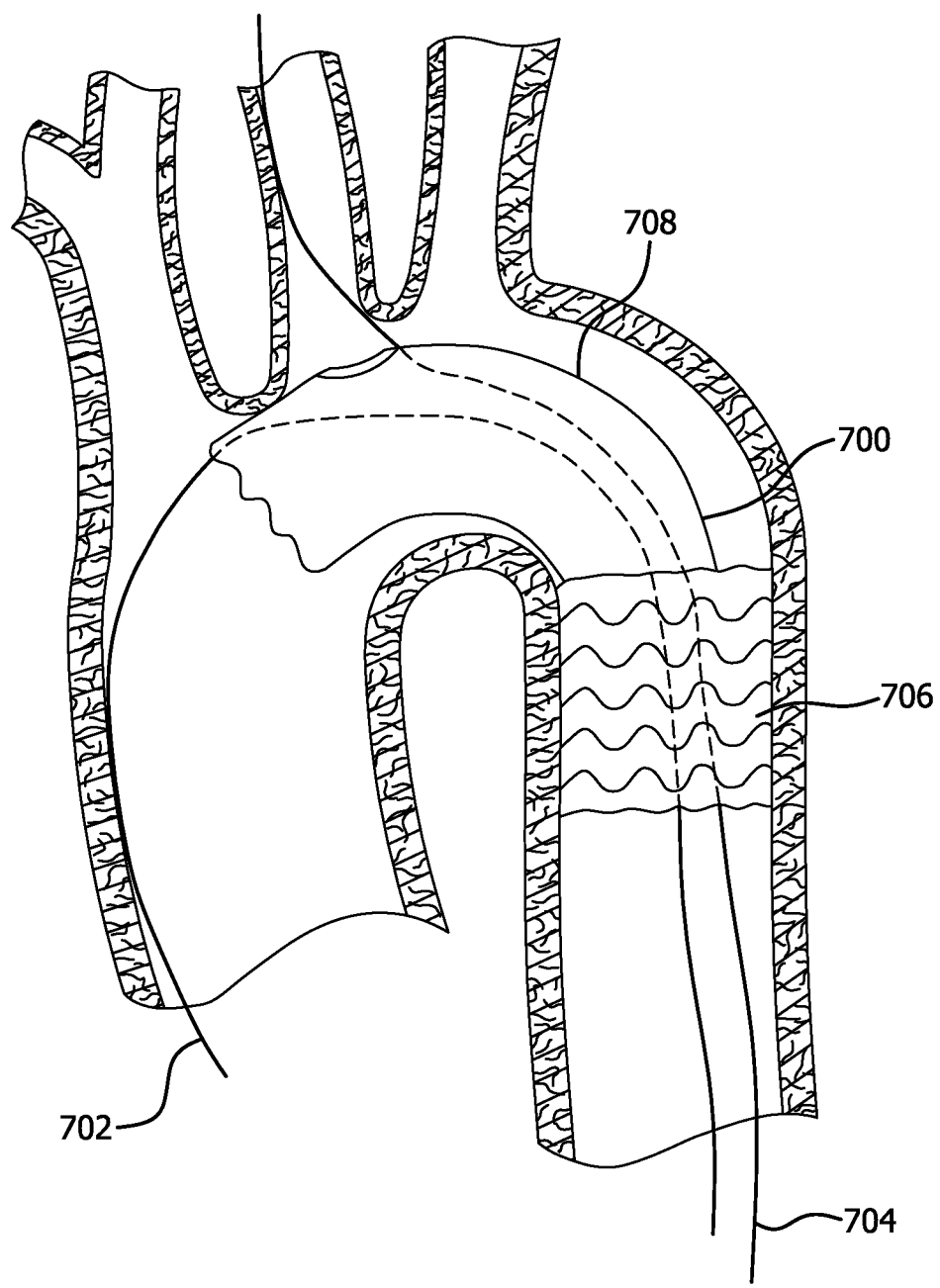
FIG. 7 illustrates a cross-sectional view of a descending stent-graft deployed within an aortic arch.

Referring now to FIG. 7, a descending stent-graft 700 can be deployed, as discussed above, from a catheter that rides over or follows a guidewire. In addition, a stent-graft 700 can be deployed from a constrained diameter based upon a determination that the stent-graft 700 is seated on a guidewire 702 and/or 704 at a position suitable to deployment, and in a deployed configuration, a trunk portion 706 of a stent-graft 700 may make contact with a luminal wall of the descending aorta. Further, in various embodiments, a trunk portion 706 of a stent-graft 700 may exert a pressure against the luminal wall of the descending aorta or otherwise couple the stent-graft 700 to the luminal wall.

Further, as discussed above, a reduced diameter portion 708 of a descending stent-graft 700 may not make contact with a luminal wall of an aortic arch. For instance, a reduced diameter portion 708 may extend through a portion of an aortic arch but leave room between an abluminal wall of the reduced diameter portion 708 and a luminal wall of the arch.

Figure 8:
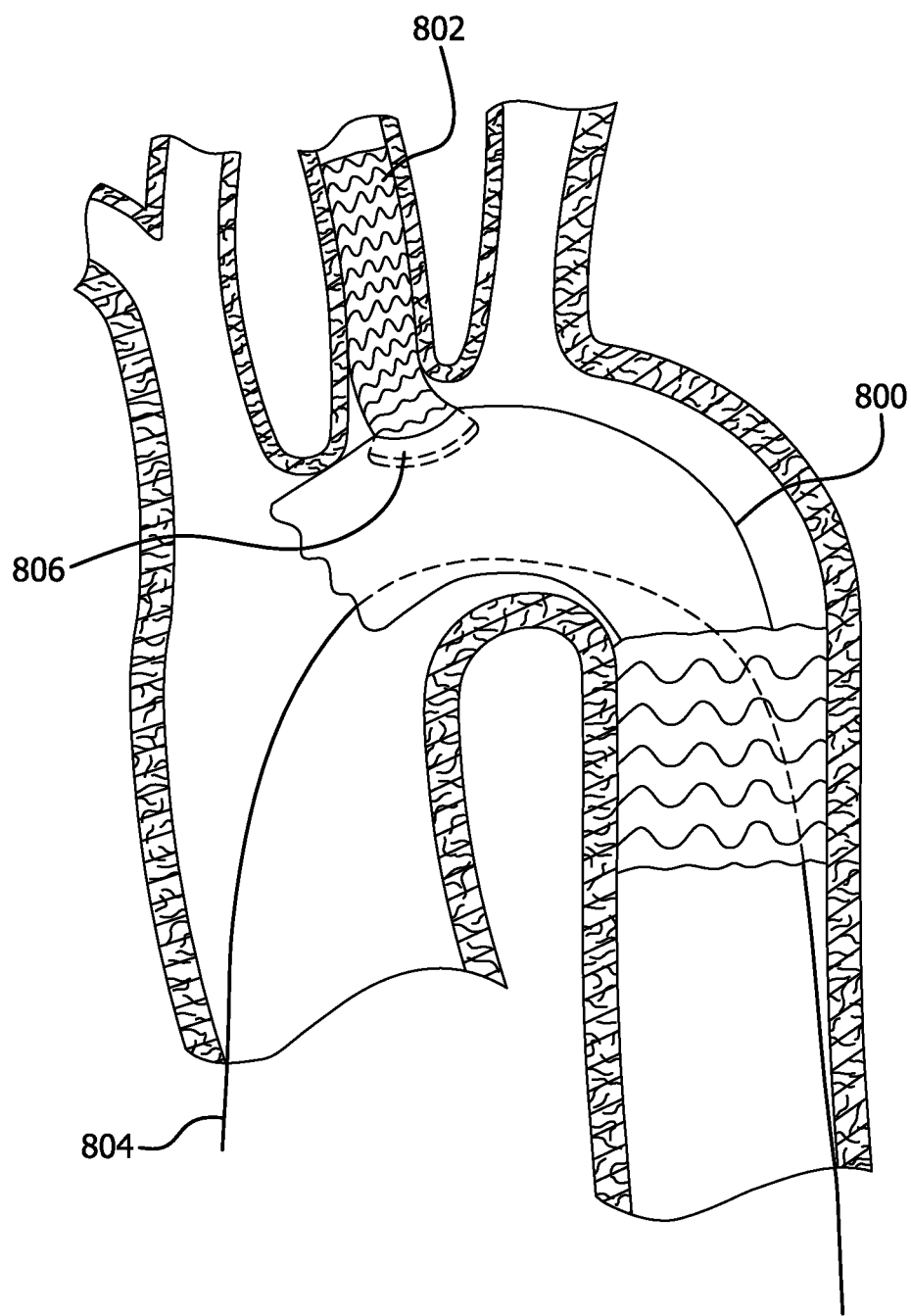
FIG. 8 illustrates a cross-sectional view of a side-branch stent-graft deployed within a left common carotid artery of an aortic arch and coupled to a descending stent-graft.

As shown at FIG. 8, a side-branch stent-graft 802 can be coupled to a descending stent-graft 800. For example, a side-branch stent-graft 802 can be advanced over a side-branch guidewire and into a side-branch vessel. Further, in various embodiments, a side-branch stent-graft 802 can be advanced in a constrained diameter through a fenestration in a deployed (or unconstrained) descending stent-graft 800 and released from this constrained diameter once in position within a side-branch vessel. In various embodiments, a side-branch stent-graft 802 may deploy to an unconstrained diameter that is substantially equal to a luminal diameter of a side-branch vessel. In addition, as discussed above, a cuff 806 included with a side-branch stent-graft 802 may crumple or fold during deployment to form a seal between a fenestration in a descending stent-graft 800 and the side-branch stent-graft 802.

Therefore, a side-branch stent-graft 802 can be implanted within a side-branch vessel and coupled to a descending stent-graft 800 such that a fenestration in the side-branch stent-graft 802 is not required to precisely align with an ostium of the side-branch vessel. Rather, the gap or space between a reduced diameter portion of the descending stent-graft 800 and the wall of the aortic arch may permit a physician to manipulate and/or maneuver a side-branch stent-graft 802 within the arch during implantation so that the stent-graft 802 is nevertheless made to cannulate a side-branch vessel as shown.

Figure 9:
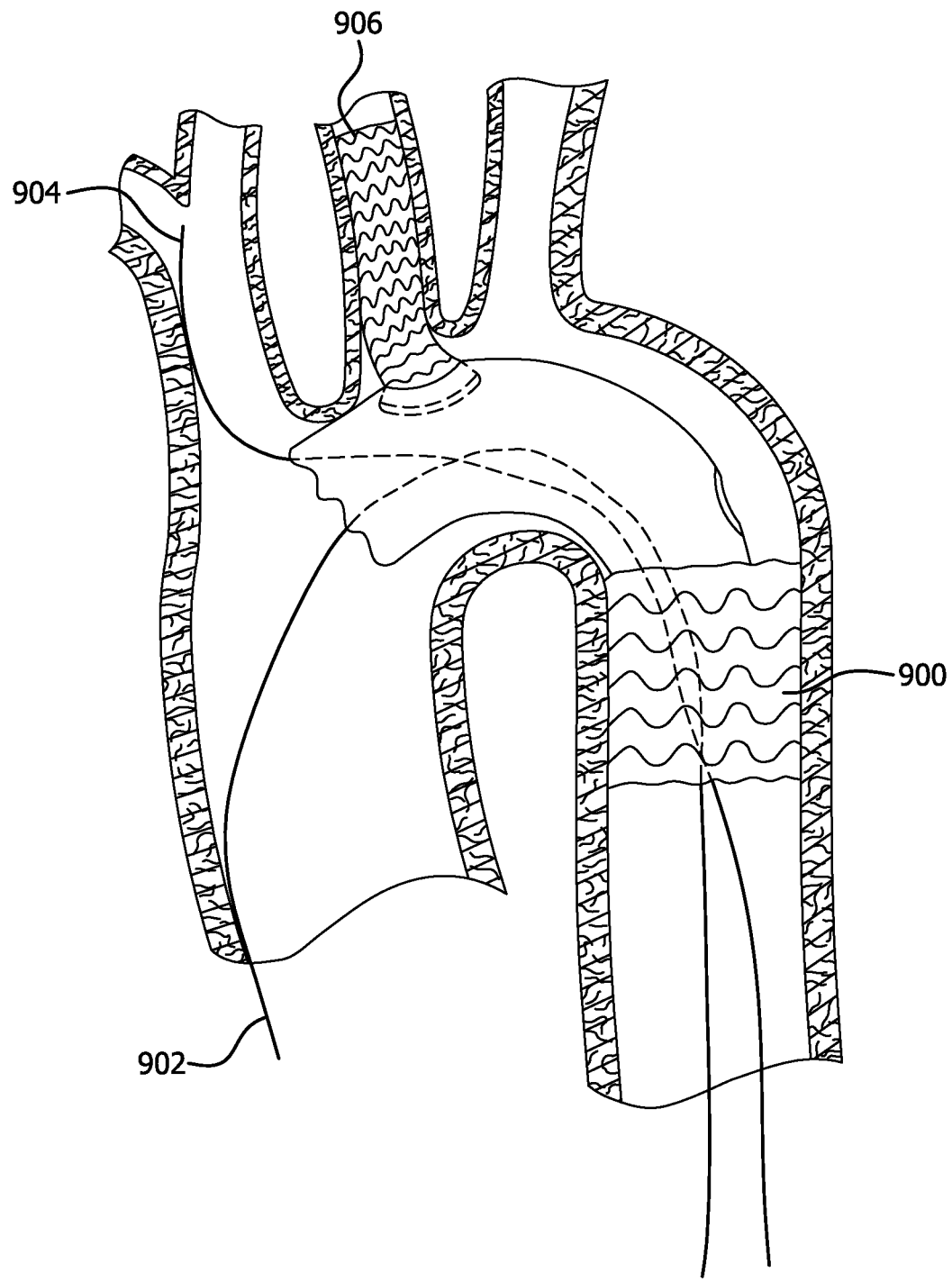
FIG. 9 illustrates a cross-sectional view of an innominate artery of an aortic arch precannulated by a guidewire.

Referring now to FIG. 9, a side-branch guidewire 904 can be advanced or repositioned (e.g., after deployment of a first side-branch stent-graft 906 within a first side-branch vessel) to precannulate an unimplanted side-branch vessel. For instance, as shown, a side-branch guidewire 904 can be advanced to precannulate an innominate artery. Further, as discussed above, a side-branch guidewire 904 can be advanced into a side-branch vessel, such as an innominate artery, such that the side-branch guidewire 904 makes contact with a luminal wall of the side-branch vessel.

Figure 10:
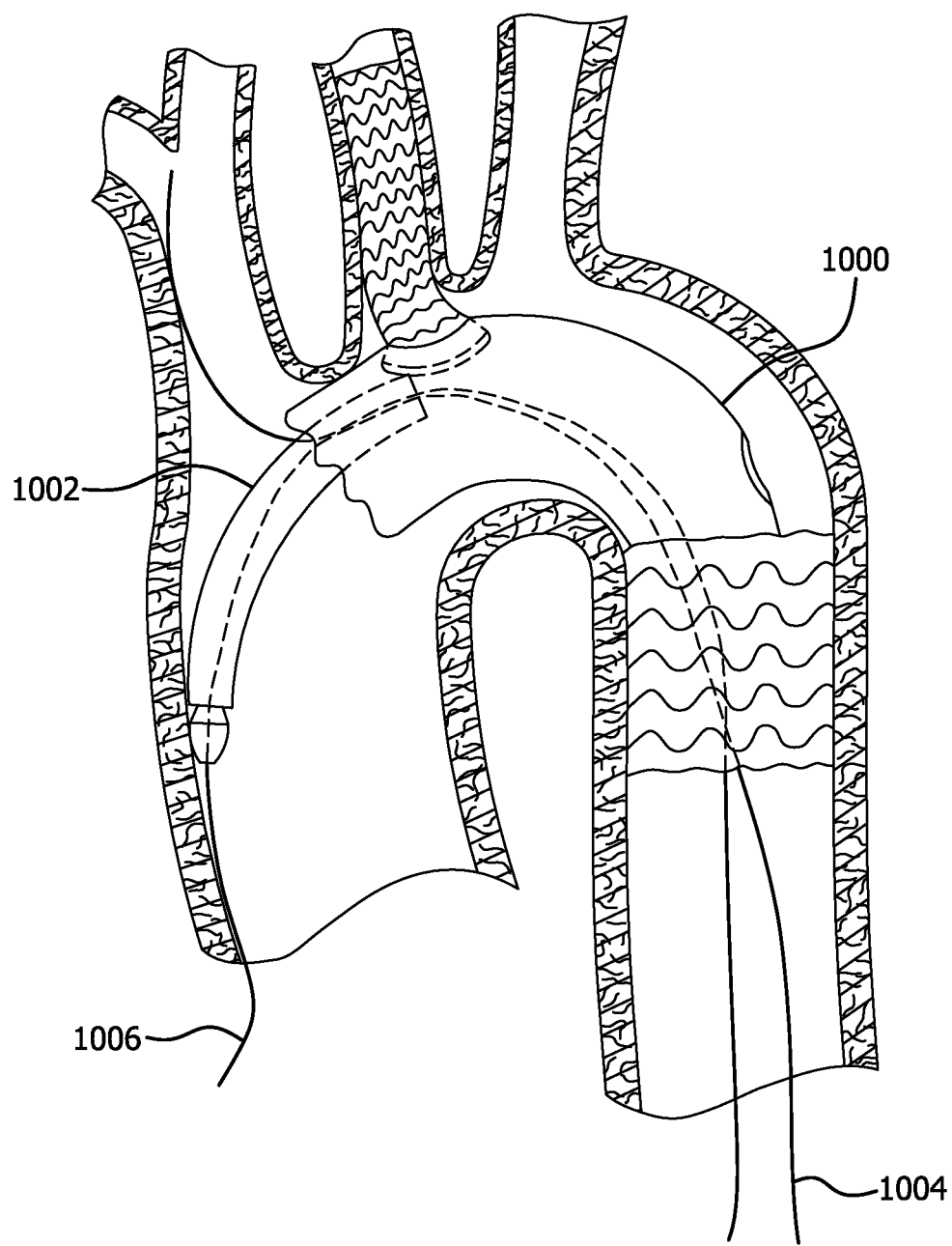
FIG. 10 illustrates a cross-sectional view of an aortic arch receiving an ascending stent-graft.

Accordingly, with reference now to FIG. 10, a main stent-graft, such as an ascending stent-graft 1002 can be advanced in a constrained diameter through a deployed descending stent-graft 1000 along a main guidewire 1006 and/or along a side-branch guidewire 1004. In various embodiments, an ascending stent-graft 1002 can be advanced along a guidewire 1004 and/or 1006 such that a trunk portion of the stent-graft 1002 is advanced distally to a proximal reduced diameter portion. In other words, an ascending stent-graft 1002 can be loaded on a guidewire by a physician such that a trunk portion of the ascending stent-graft 1002 is distal to the physician.

Further, as discussed above with reference to a descending stent-graft, an ascending stent-graft 1002 can be advanced along a guidewire 1004 and/or 1006 until a resistance to continued advancement is encountered, e.g., due to a pressure exerted against the ascending stent-graft 1002 by the side-branch guidewire 1004, which can be deployed into a side-branch vessel and result in contact between the side-branch guidewire 1004 and a wall of a fenestration. One or more radiopaque markers may also be coupled to an ascending stent-graft 1002, and these may also help to position the stent-graft 1002 in a suitable portion of an ascending aortic arch.

Figure 11:
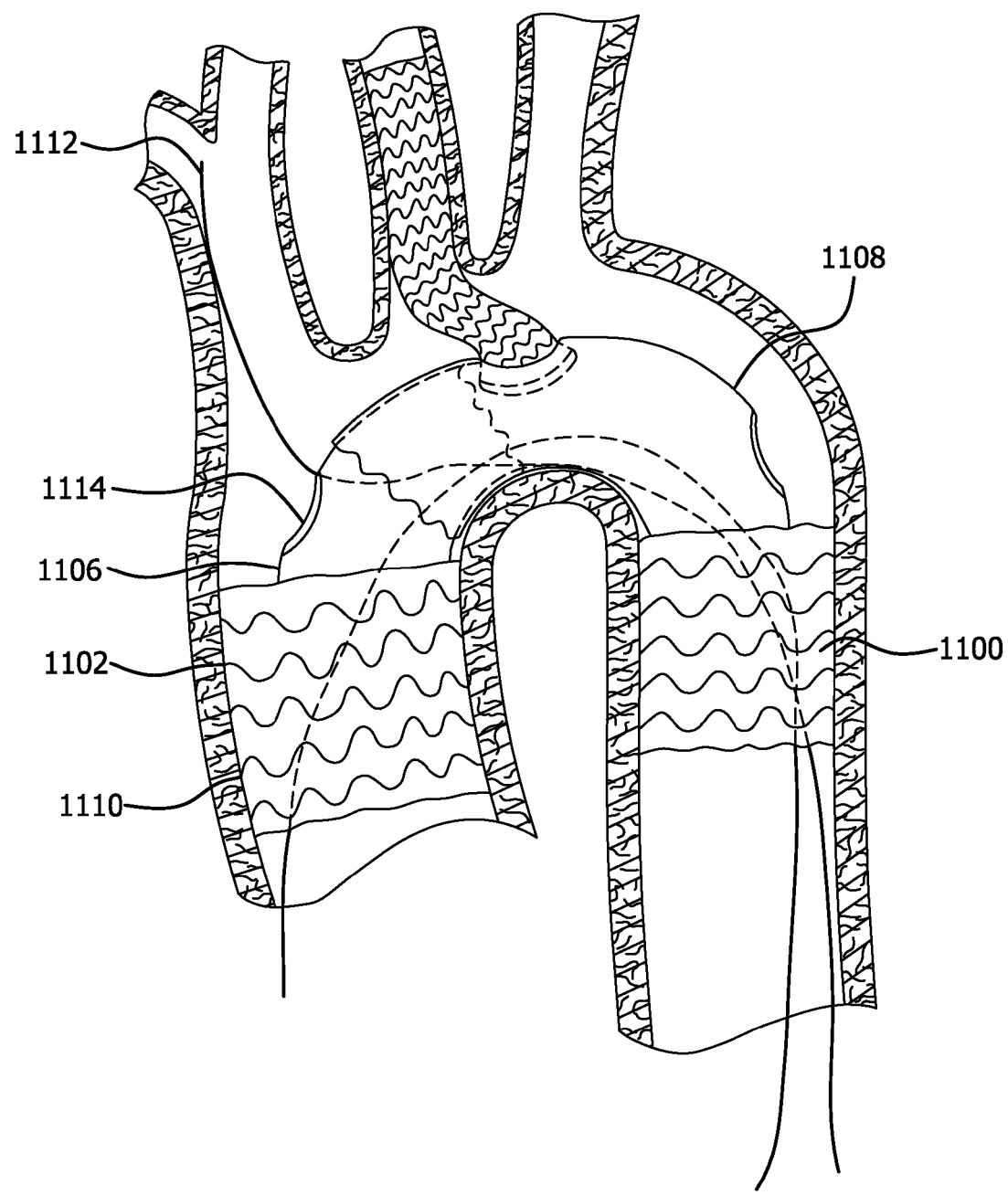
FIG. 11 illustrates a cross-sectional view of an ascending stent-graft deployed within an aortic arch.

Further, with attention to FIG. 11, an ascending stent-graft 1102 can be expanded from a constrained diameter proximate to or located within an ascending portion of an aortic arch. In addition, in various embodiments, an ascending stent-graft 1102 can be deployed within an aortic arch such that an abluminal wall of a reduced diameter portion 1106 of an ascending stent-graft 1102 makes contact with and is secured within a luminal wall of a reduced diameter portion 1108 of a descending stent-graft 1100. Thus, in a deployed configuration, an ascending stent-graft 1102 may couple to a descending stent-graft 1100 to form an arch within an aortic arch. In addition, as discussed herein, a reduced diameter portion 1106 of an ascending stent-graft 1102 may expand to a deployed diameter that is less than a diameter of an aortic arch, while a trunk portion 1110 of an ascending stent-graft 1102 may expand to a deployed diameter that is substantially equal to a diameter of an aortic arch. Therefore, in various embodiments, a trunk portion 1110 of an ascending stent-graft 1102 may secure an ascending stent-graft 1102 within an aortic arch through pressure against and/or contact with the arch.

Figure 12:
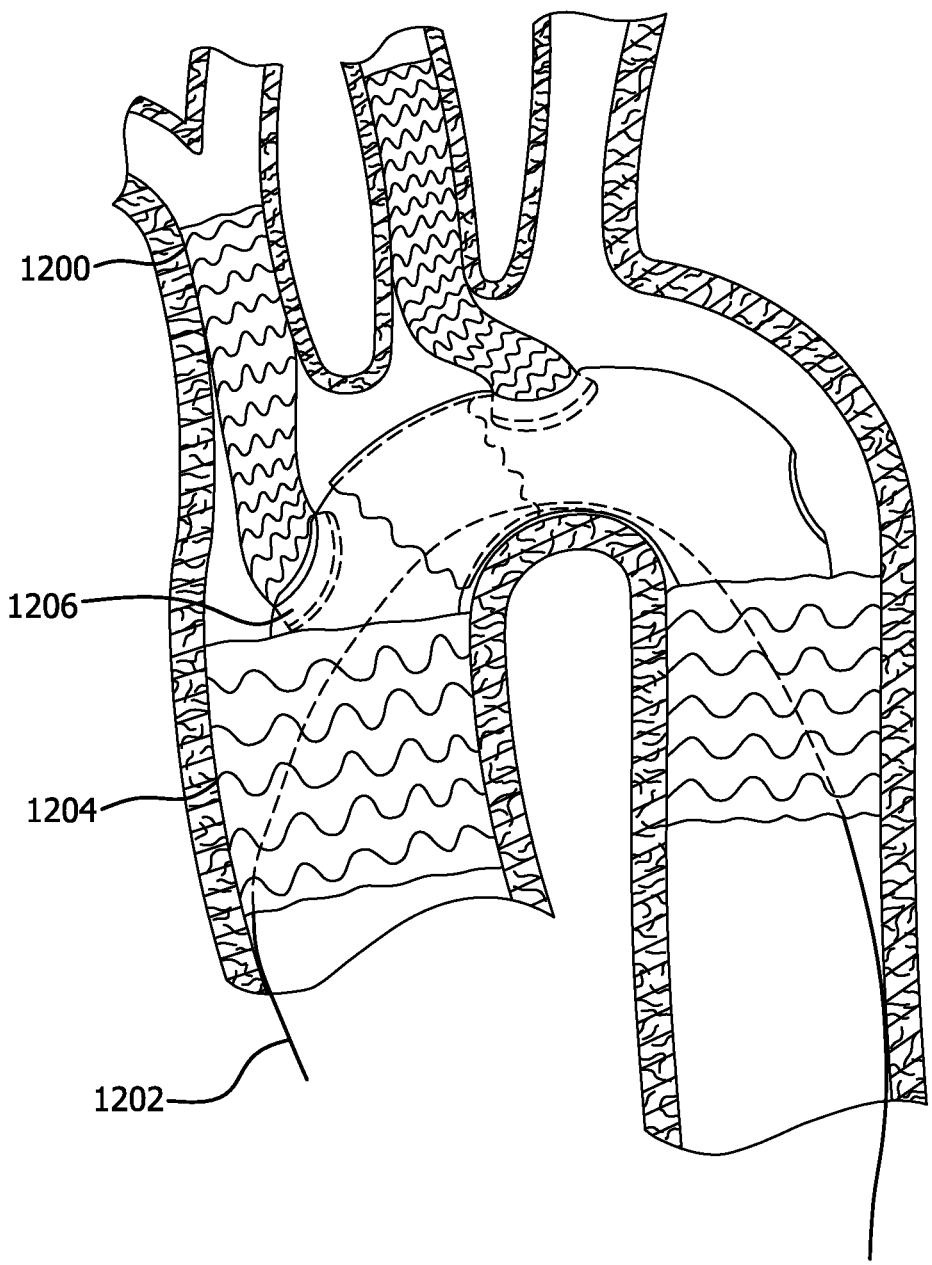
FIG. 12 illustrates a cross-sectional view of a side-branch stent-graft deployed within an innominate artery of an aortic arch.

With continuing reference to FIG. 11, as shown, a side-branch guidewire 1112 may extend through a fenestration 1114 made in an ascending stent-graft and into a side-branch vessel, such as for example, an innominate artery. Accordingly, with attention now to FIG. 12, a side-branch stent-graft 1200 can be advanced along a side-branch guidewire and through a fenestration made in an ascending stent-graft 1204 to cannulate a side-branch vessel, such as an innominate artery. In addition, as discussed herein, a cuff 1206 included with a side-branch stent-graft 1200 may crumple or fold during deployment to form a seal between a fenestration in an ascending stent-graft 1204 and the side-branch stent-graft 1200.

In various embodiments, a side-branch stent-graft 1200 may deploy to an unconstrained diameter that is substantially equal to a luminal diameter of a side-branch vessel wall. Further, as discussed above, a side-branch stent-graft 1200 can be implanted within a side-branch vessel and coupled to an ascending stent-graft 1204 such that a fenestration in the side-branch stent-graft 1200 is not required to precisely align with an ostium of the side-branch vessel.

Figure 13:
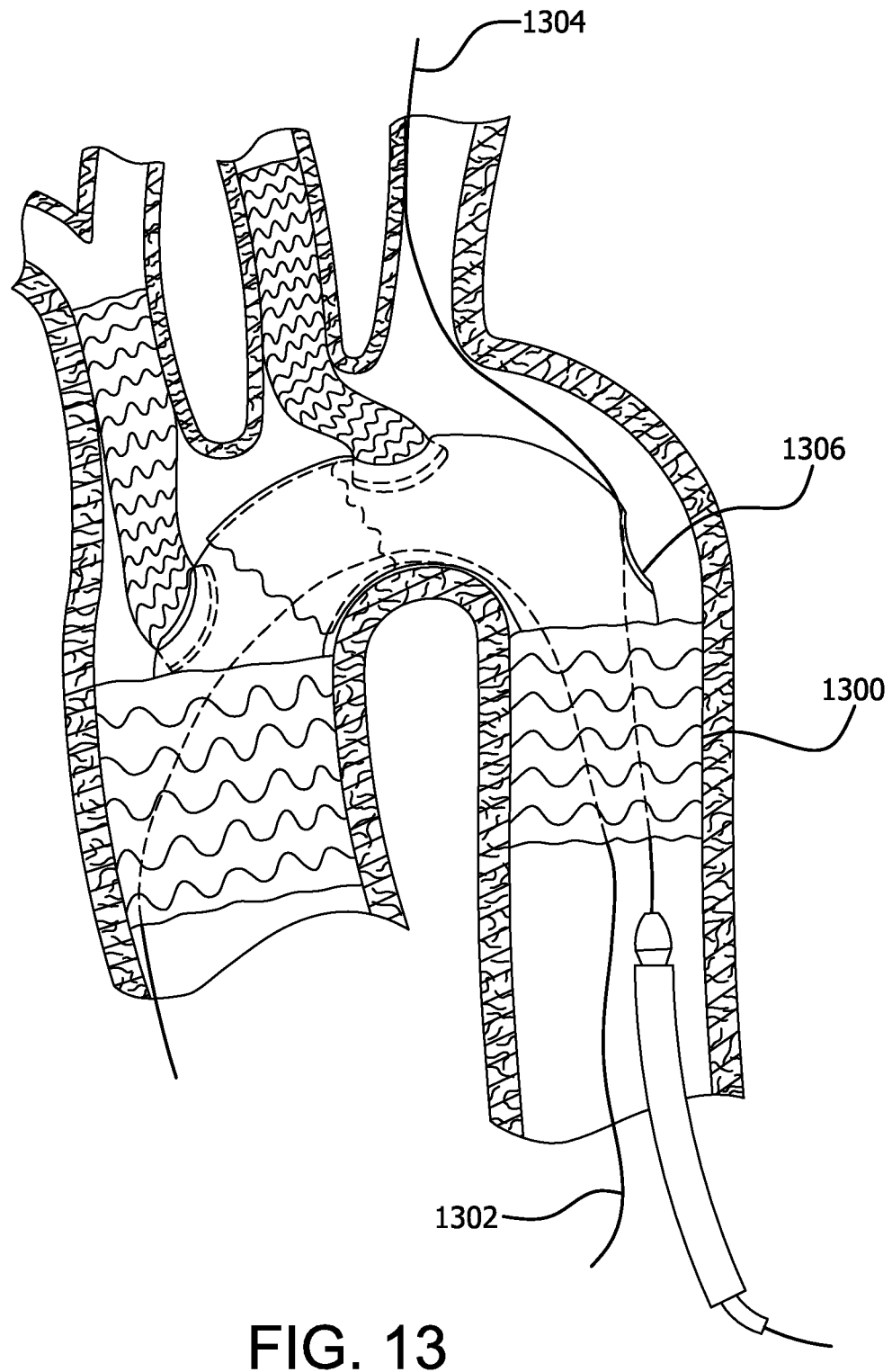
FIG. 13 illustrates a cross-sectional view of a left subclavian artery of an aortic arch precannulated by a guidewire.

Turning now to FIG. 13, a side-branch guidewire 1304 can be advanced or repositioned (e.g., after deployment of a second side-branch stent-graft 1200 within a second side-branch vessel) to precannulate an unimplanted side-branch vessel. For instance, as shown, a side-branch guidewire 1304 can be advanced to precannulate a left subclavian artery. Further, as discussed above, a side-branch guidewire 1304 can be advanced into a side-branch vessel, such as a left subclavian artery, such that the side-branch guidewire 1304 makes contact with a luminal wall of the side-branch vessel. In addition, a side-branch guidewire 1304 may advance through a fenestration 1306 in a descending stent-graft 1300 as it precannulates an unimplanted side-branch vessel.

Figure 14:
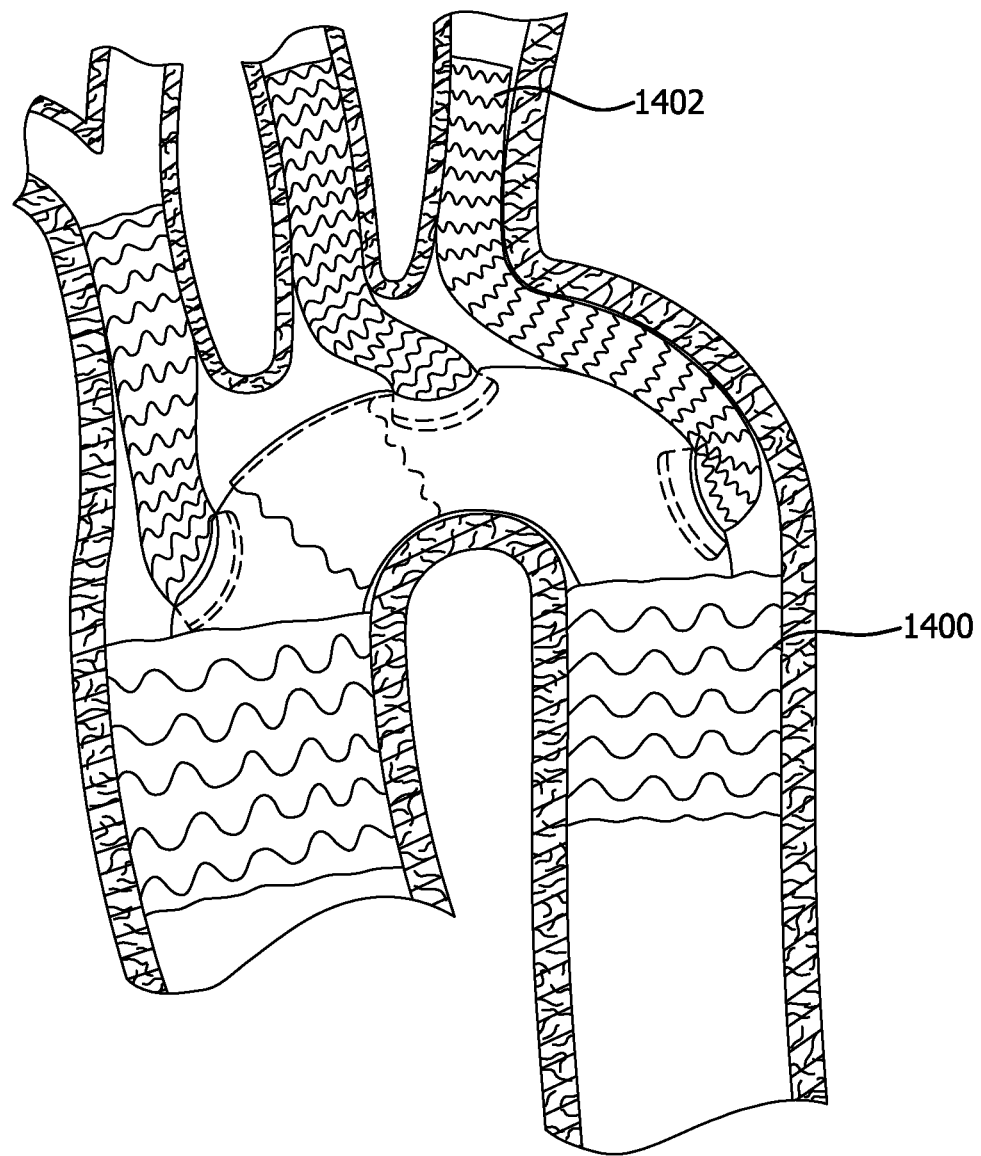
FIG. 14 illustrates a cross-sectional view of a side-branch stent-graft deployed within a left subclavian artery of an aortic arch.

Accordingly, with reference to FIG. 14, a side-branch stent-graft 1402 can be advanced along a side-branch guidewire and deployed through a fenestration in a descending stent-graft 1400 within a side-branch vessel, such as the left subclavian artery. In addition, as discussed above, a side-branch stent-graft 1402 can be implanted within a side-branch vessel and coupled to a descending stent-graft 1400 such that a fenestration in the side-branch stent-graft 1402 is not required to precisely align with an ostium of the side-branch vessel. On the contrary, in various embodiments and as shown, a fenestration made in a descending (and/or ascending) stent-graft 1400 may not at all align with an ostium of a side-branch artery.

Figure 15A:
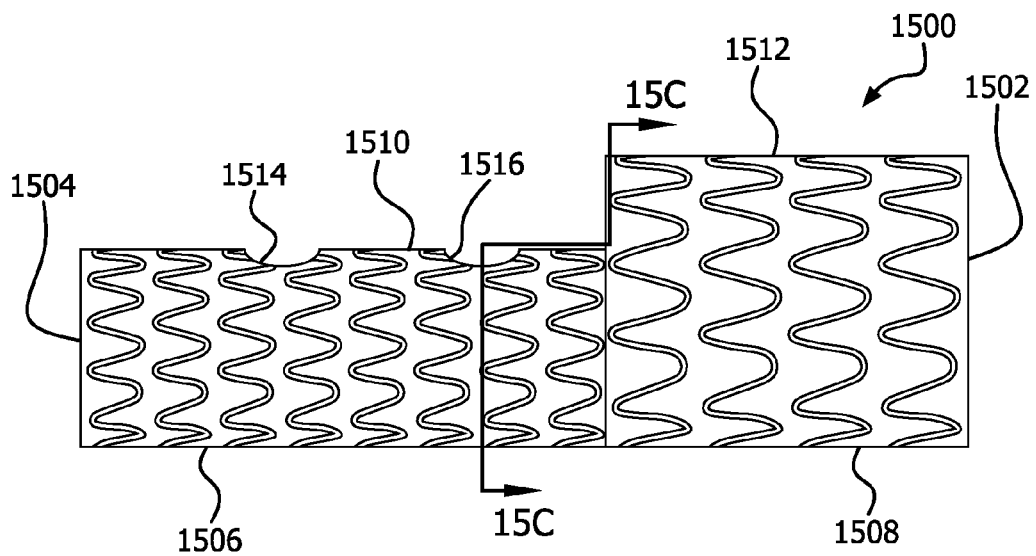
FIG. 15A illustrates a main stent-graft having a reduced diameter portion and a trunk portion.
Figure 15B:
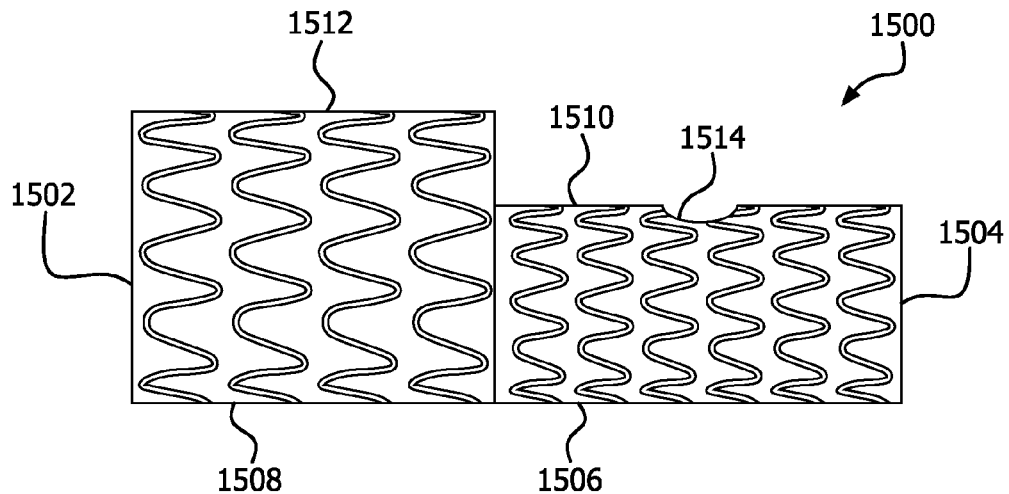
FIG. 15B illustrates a main stent-graft having a reduced diameter portion and a trunk portion.
Figure 15C:
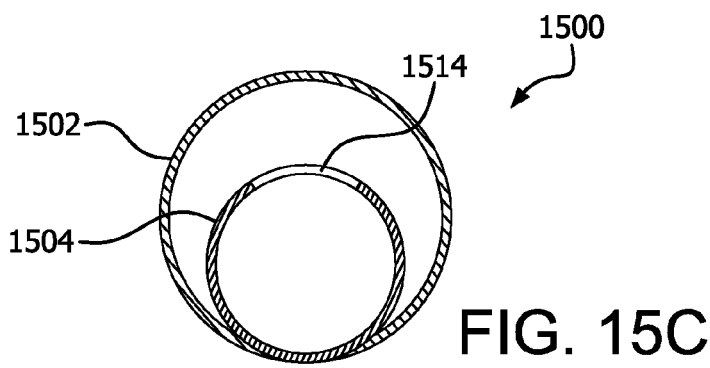
FIG. 15C illustrates a cross-sectional view of a main stent-graft having a reduced diameter portion and a trunk portion.

In various embodiments, a main stent-graft can be formed as shown at FIGS. 15A-15C. More particularly, as discussed herein, a main stent-graft 1500 can comprise a trunk portion 1502 and a reduced diameter portion 1504. A reduced diameter portion 1504 may, as shown, abut or sit adjacent to a trunk portion 1502 so that the reduced diameter portion 1504 is concentrically offset from and/or extends axially into and/or away from the trunk portion 1502. Thus, in various embodiments, a reduced diameter portion 1504 may not be concentric with a trunk portion 1502. Rather, a base portion 1506 of a reduced diameter portion 1504 may extend substantially tangentially to a base portion 1508 of a trunk portion 1502, while an upper portion 1510 of a reduced diameter portion 1504 may extend from a trunk portion 1502 at a level below or inferior to an upper portion 1512 of the trunk portion 1502. In various embodiments, a reduced diameter portion 1504 may recede abruptly (e.g., at a substantially ninety degree angle) from a trunk portion 1502. Similarly, in various embodiments, a reduced diameter portion 1504 may recede or taper at a more obtuse angle from a trunk portion 1502.

Further, in various embodiments, one or more fenestrations 1514 and/or 1516 can be formed in a main stent-graft 1500 substantially opposite a base portion (e.g., portions 1506 and/or 1508) of the stent-graft 1500. For example, in various embodiments, a fenestration 1514 and/or 1516 can be formed in a reduced diameter portion 1504 substantially opposite a base portion 1506 of the reduced diameter portion 1504.

Thus, as discussed herein, a reduced diameter portion 1504 can be implanted within a body lumen such that a side-branch stent-graft has room to maneuver between the body lumen wall and the outer surface of the reduced diameter portion 1504. Further, because a reduced diameter portion 1502 may not be concentric with a trunk portion 1502, an optimal or maximum amount of space can be provided between a luminal wall and the reduced diameter portion 1502 for maneuvering a side-branch stent-graft.

Figure 16:
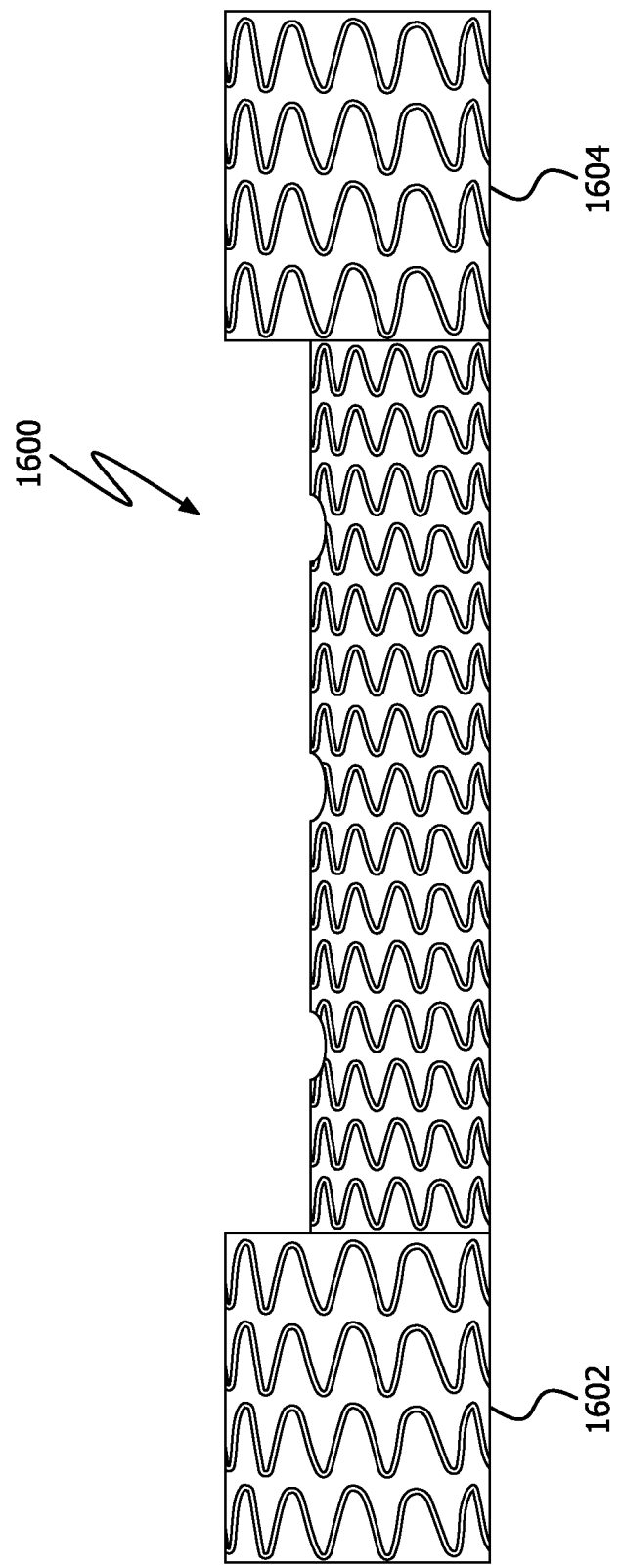
FIG. 16 illustrates a unitary endoprosthesis.

With reference now to FIG. 16, in various embodiments, an ascending stent-graft 1602 can be coupled to or integral with a descending stent-graft 1604 a priori of implantation of each stent-graft 1602 and 1604 within a body lumen. Thus, although in certain embodiments, an ascending stent-graft can be coupled during implantation to a descending stent-graft, each stent-graft 1602 and/or 1604 may also be implanted as an integral or unitary component. Where an endoprosthesis 1600 comprises such a unitary component, the endoprosthesis can be implanted, as described herein, with the use of one or more guidewires (e.g., a main guidewire, a side-branch guidewire, and the like), and one or more side-branch stent-grafts coupled to the ascending and/or descending stent-grafts 1602 and 1604 through one or more fenestrations in the device 1500. Further, although such a unitary endoprosthesis 1600 may not be implanted in separate pieces, as described elsewhere herein, one or more reduced diameter portions may nevertheless telescope into and/or extend tangentially into and/or away from one or more trunk portions, as described herein.

Accordingly, in various embodiments, a unitary endoprosthesis 1600 can be implanted within a body lumen to eliminate or reduce a risk of disengagement (e.g., during implantation) of a descending stent-graft from an ascending stent-graft. Similarly, with further regard to such a unitary endoprosthesis 1600, in various embodiments, the spacing between one or more fenestrations can be preset or predetermined, and it may be necessary, where fewer side-branch vessels are to be cannulated than the number of fenestrations in the endoprosthesis 1600, to occlude or block one or more unused fenestrations to prevent perfusion of blood and/or other fluids through these unused fenestrations.

On the other hand, and with regard to an endoprosthesis comprising an ascending stent-graft and a descending stent-graft that are coupled or engaged to each other during implantation (i.e., a non-unitary endoprosthesis), a spacing between one or more fenestrations may be adjusted prior to and/or during implantation by adjusting an overlap between each stent-graft. Moreover, each fenestration comprising a non-unitary endoprosthesis can be rotated within a body lumen so that the fenestration can be ideally situated. Further, a reduced diameter portion of a non-unitary endoprosthesis can be elongated or shortened during implantation to more precisely conform to a patient's individual anatomy. This can be accomplished by varying an overlap between an ascending reduced diameter portion and a descending reduced diameter portion. Variation in the overlap between an ascending reduced diameter portion and a descending reduced diameter portion may also permit a physician to vary a number of fenestrations that are used during implantation of a non-unitary endoprosthesis without the need to independently occlude unused fenestrations.

Figure 17:
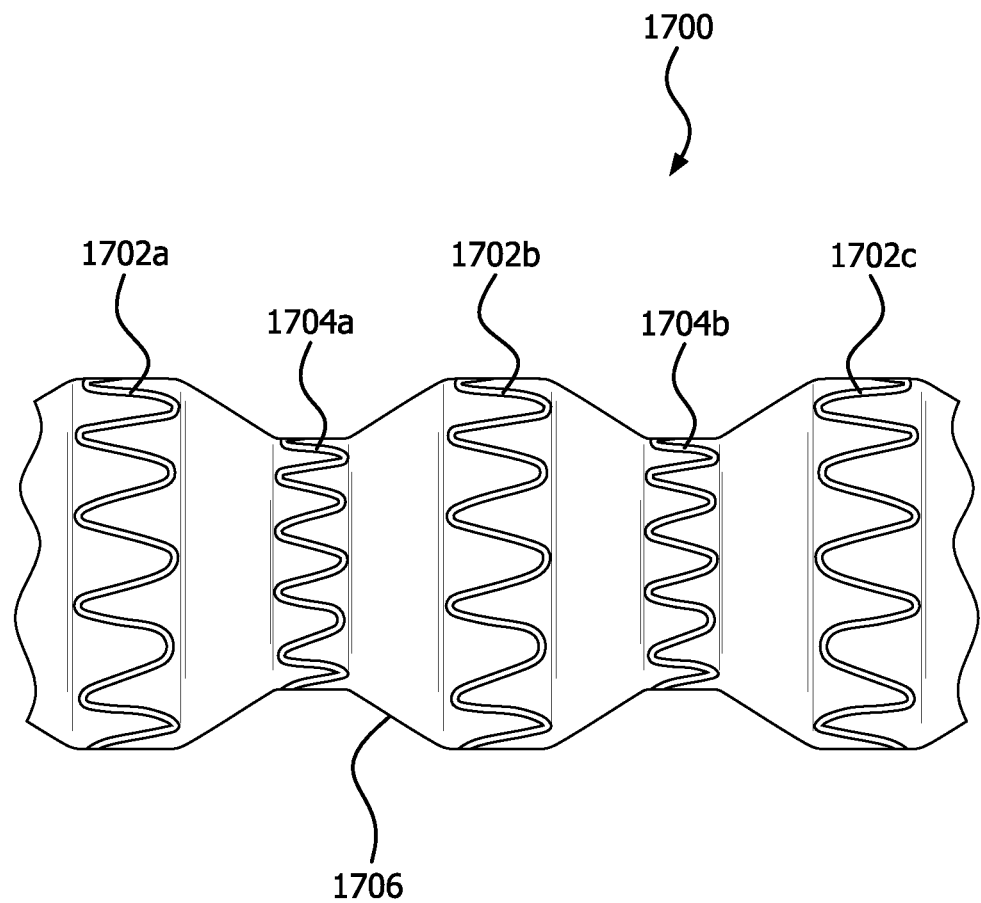
FIG. 17 illustrates a perspective view of a main or side-branch stent-graft capable of extending telescopically.

With reference now to FIG. 17, in various embodiments, a main or side-branch stent-graft 1700 can comprise a plurality of stent-rings coupled by a tube or tubular sheet of graft material. For example, a main or side-branch stent-graft 1700 can comprise a first plurality of stent-rings, e.g., 1702a, 1702b, 1702c, having a first diameter and a second plurality of stent-rings, e.g., 1704a 1704b, having a second diameter. The first diameter can be larger than the second diameter. One or more stent-rings from the first plurality of stent-rings can be interleaved with one or more stent-rings from the second plurality of stent-rings, so that a main or side-branch stent-graft 1700 comprises an alternating series of one or more first diameter and one or more second diameter stent-rings (e.g., first diameter ring, second diameter ring, first diameter ring, second diameter ring, etc.).

In addition to facilitating graft placement with tortuous vasculature without kinking, this construction allows a main or side-branch stent-graft 1700 to vary in axial length or configuration. In particular, the stent-rings 1702a-c and/or 1704a-b comprising a main or side-branch stent-graft 1700 can be spaced such that the graft material 1706 connecting each stent ring can be crumpled or collected in a bunched, accordion-like, or bellows-like configuration. In some embodiments, a larger diameter stent ring can override or overlap a smaller diameter stent ring in a bunched configuration. Thus, a main or side-branch stent-graft 1700 can be made relatively short.

In addition, a main or side-branch stent-graft 1700 can telescope from a bunched configuration. In particular, the distance between stent-rings 1702a-c and/or 1704a-b comprising a main or side-branch stent-graft 1700 can be increased, so that the graft material 1706 connecting each stent ring extends from the bunched configuration. Thus, as the distance between stent rings increases, the stent-graft 1700 can telescope from a bunched configuration to a longer, telescoped, configuration.

In various embodiments, the graft material 1706 coupling one or more stent rings can, as discussed below, comprise an ePTFE material. In addition, the graft material may resist radial constriction, or "necking," as the graft material is stretched (e.g., as a main or side-branch stent-graft 1700 is deployed to a telescoped configuration). In addition, in various embodiments, the graft material 1706 may not neck at all.

Therefore, in operation, and with returning reference to FIGS. 15A-15C, a reduced diameter portion 1504 of a stent-graft 1500 can assume a telescoped configuration. In particular, the stent rings comprising the reduced diameter portion 1504 can extend or telescope away from one another, so that the stent-graft telescopes or lengthens.

Moreover, in a bunched configuration, a fenestration 1514 and/or 1516 can be occluded or blocked by ePTFE folds in the graft material coupling and/or covering adjacent stent rings. However, one or more of these fenestrations 1514 and/or 1516 can be exposed or opened as a stent-graft 1500 telescopes. Thus, a stent-graft can lengthen and/or shorten between bunched (or partially bunched) and telescoped (or partially telescoped) configurations. This can allow a physician to occlude, or open, a number of fenestrations 1514 and/or 1516 needed to treat a particular patient. A telescoping stent-graft 1500 therefore permits a physician to tailor a stent-graft to the anatomy of an individual patient.

In various embodiments, the telescoping stent-grafts described herein are further very easily adjusted between bunched and telescoped configurations. In fact, the force necessary to lengthen or shorten these stent grafts can be applied, in various embodiments, by a guidewire or guidewire catheter, as described herein. Thus, during deployment, a physician may adjust a length of a stent-graft by applying a slight distally or proximally directed force to the stent-graft. The telescoping stent-grafts may therefore adjust quite easily in situ.

The devices and methods described herein thus enable implantation of one or more stent-grafts within an aortic arch. In addition, the flexibility and maneuverability afforded by these devices, as discussed herein, permits the universal application of these devices and methods to a variety of aortic arches. In other words, the endoprostheses disclosed herein can be used as off the shelf (as opposed to custom) components to treat a large number of anatomically diverse patients.

A graft comprising any of the grafts and/or stent-grafts described above can be made up of any material which is suitable for use as a graft in the chosen body lumen. A graft can comprise one or a variety of materials. Furthermore, a graft can comprise multiple layers of material, which can be the same material or different material. Although a graft may have several layers of material, the graft may have a layer that is formed into a tube (innermost tube) and an outermost layer that is formed into a tube (outermost tube). In some embodiments, a graft can be fenestrated with a fenestration tool.

Many graft materials are known, and in various embodiments, these materials can be used in combination and assembled together to comprise a graft. These materials can be further extruded, coated and/or formed from wrapped films, and/or a combination thereof. Polymeric materials, biodegradable materials, and/or natural materials can be used for specific applications.

In various embodiments, a graft can comprise synthetic polymers including nylon, polyacrylamide, polycarbonate, polyformaldehyde, polymethylmethacrylate, polytetrafluoroethylene, polytrifluorochlorethylene, polyvinylchloride, polyurethane, elastomeric organosilicon polymers, polyethylene, polypropylene, polyurethane, polyglycolic acid, polyesters, polyamides, their mixtures, blends, and copolymers. In a variety of embodiments, a graft can be made from a class of polyesters such as polyethylene terephthalate including DACRON® and MYLAR® and polyaramids such as KEVLAR®, polyfluorocarbons such as polytetrafluoroethylene (PTFE) with and without copolymerized hexafluoropropylene (TEFLON® or GORE-TEX®), and porous or nonporous polyurethanes. Further, in a variety of embodiments, a graft can comprise expanded fluorocarbon polymers (especially PTFE), materials described in British. Pat. Nos. 1,355,373; 1,506,432; or 1,506,432 or in U.S. Pat. No. 3,953,566; 4,187,390; or 5,276,276, all of which are incorporated by reference in their entireties.

In various embodiments, fluoropolymers can include polytetrafluoroethylene (PTFE), expanded PTFE (ePTFE), fluorinated ethylene propylene (FEP), copolymers of tetrafluoroethylene (TFE) and perfluoro (propyl vinyl ether) (PEA), homopolymers of polychlorotrifluoroethylene (PCTFE), and its copolymers with TFE, ethylene-chlorotrifluoroethylene (ECTFE), copolymers of ethylene-tetrafluoroethylene (ETFE), polyvinylidene fluoride (PVDF), and polyvinylfluoride (PVF). In various embodiments, a graft can comprise any combination of the materials listed above. Further, in various embodiments, a graft can be substantially impermeable and/or permeable to bodily fluids. A substantially impermeable graft can be made from materials that are substantially impermeable to bodily fluids or can be constructed from permeable materials treated or manufactured to be substantially impermeable to bodily fluids (e.g. by layering different types of materials described above or known in the art). In various embodiments, a stent-graft and/or a side-branch stent-graft, as described above, can be made from any combination of the materials described above, including ePTFE.

Any stent, including stent and/or stent members can be generally cylindrical when restrained and/or when unrestrained and can comprise helically arranged undulations having a plurality of helical turns. In a variety of embodiments, undulations can be aligned so that they are "in-phase" with each other. More specifically, undulations can comprise apices in opposing first and second directions. When these undulations are in-phase, apices in adjacent helical turns are aligned so that apices can be displaced into respective apices of a corresponding undulation in an adjacent helical turn. In certain embodiments, undulations may have a sinusoidal shape, a U shape, a V shape, and/or an ovaloid shape, as described in U.S. Pat. No. 6,042,605 and U.S. Pat. No. 6,042,605, both of which are incorporated by reference herein in their entireties.

In various embodiments, a stent can be fabricated from a variety of biocompatible materials including commonly known materials (or combinations of materials) used in the manufacture of implantable medical devices. Such materials can include 316L stainless steel, cobalt-chromium-nickel-molybdenum-iron alloy ("cobalt-chromium"), other cobalt alloys such as L605, tantalum, nitinol, or other biocompatible metals. In some embodiments, any stent and/or stent-graft described herein can comprise a balloon expandable stent and/or stent-graft and/or a self-expanding stent and/or stent-graft. Further, in certain embodiments, a stent can comprise a wire wound stent, which may or may not comprise undulations.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size, and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. An endoprosthetic assembly for treating a main vessel and at least one branch vessel extending from the main vessel, the endoprosthetic assembly comprising:
a first expandable device and a second expandable device, each having a generally tubular shaped wall comprising a trunk portion configured for engaging the main vessel;
reduced diameter portions of each of the first and second devices having reduced diameters relative to their respective trunk portions, at least one of the reduced diameter portions being concentrically offset from a trunk portion to which it is coupled, and the first and second devices being configured to engage each other telescopically; and
at least one branch for treating the at least one branch vessel and extending through a fenestration in one of the reduced diameter portions.

2. The endoprosthetic assembly as in claim 1 including a second branch through a second fenestration formed in the reduced diameter portion of the other of the first and second expandable devices.

3. The endoprosthetic assembly as in claim 2 including a third branch through a third fenestration formed in the reduced diameter portion of one of the first and second expandable devices.

4. The endoprosthetic assembly as in claim 1 including visually distinct radiopaque or echogenic markers on each of the first and second expandable devices.

5. An endoprosthesis comprising:
a descending stent-graft;
an ascending stent-graft; and
a side-branch stent-graft, the descending stent-graft comprising a reduced diameter portion that, when implanted within an aortic arch, recedes from a luminal surface of the aortic arch to allow the side-branch stent-graft to be maneuvered within the aortic arch.

6. The endoprosthesis of claim 5, wherein the ascending stent-graft is capable of being coupled to the descending stent-graft.

7. The endoprosthesis of claim 5, wherein the descending stent-graft comprises a fenestration capable of being coupled to the side-branch stent-graft.

8. The endoprosthesis of claim 5, wherein the descending stent-graft comprises two fenestrations, a first fenestration capable of being coupled to the side-branch stent-graft and a second fenestration capable of being coupled to another side-branch stent-graft.

9. The endoprosthesis of claim 5, wherein the ascending stent-graft comprises a fenestration capable of being coupled to the side-branch stent-graft.

10. The endoprosthesis of claim 5, wherein the ascending stent-graft comprises a reduced diameter portion that, when implanted within an aortic arch, recedes from a luminal surface of the aortic arch to allow a side-branch stent-graft to be maneuvered within the aortic arch.

11. The endoprosthesis of claim 5, wherein each of the ascending and descending stent-grafts comprises a trunk portion and a reduced diameter portion, the reduced diameter portion coupled to the trunk portion and concentrically offset from the trunk portion.

12. A method comprising:
precannulating a side-branch artery with a guidewire prior to deploying a descending stent-graft, wherein the guidewire abuts a luminal surface of the side-branch artery to facilitate deployment of the descending stent-graft;
deploying the descending stent-graft within the descending portion of an aortic arch;
deploying an ascending stent-graft within an ascending portion of the aortic arch; and
deploying a side-branch stent-graft through a fenestration in one of the ascending stent-graft and the descending stent-graft.

13. The method of claim 12, wherein the ascending stent-graft couples to the descending stent-graft during deployment.

14. The method of claim 12, further comprising maneuvering the side-branch stent-graft within the aortic arch between the fenestration and an ostium of a side-branch artery.

15. The method of claim 12, further comprising deploying two side-branch stent-grafts through two fenestrations in the descending stent-graft and a single side-branch stent-graft through a fenestration in the ascending stent-graft.

16. The method of claim 12, further comprising precannulating the aortic arch with two guidewires prior to the deploying the descending stent-graft.

17. The method of claim 16, wherein the two guidewires extend through common entry into a femoral artery.

18. The method of claim 12, further comprising loading the ascending stent-graft on a guidewire such that a trunk portion of the ascending-stent-graft is located distal to a reduced diameter portion of the ascending stent-graft.

19. The method of claim 12, further comprising imaging one of the descending stent-graft, the ascending stent-graft and the side-branch stent-graft by way of a radiopaque marker.

20. The method of claim 12, wherein a flow through at least one side-branch stent-graft is retrograde relative to a main vessel flow.

21. The method of claim 12, further comprising deploying a balloon in one of the two side-branch stent-grafts.

22. The method of claim 12, the descending stent-graft comprising a trunk portion and a reduced diameter portion, the reduced diameter portion concentrically offset from the trunk portion.

23. The method of claim 12, the ascending stent-graft comprising a trunk portion and a reduced diameter portion, the reduced diameter portion concentrically offset from the trunk portion.

24. An endoprosthesis comprising:
a descending stent-graft;
an ascending stent-graft; and
a side-branch stent-graft, the ascending stent-graft comprising a reduced diameter portion that, when implanted within an aortic arch, recedes from a luminal surface of the aortic arch to allow the side-branch stent-graft to be maneuvered within the aortic arch.

25. An endoprosthesis comprising:
a descending stent-graft;
an ascending stent-graft; and
a side-branch stent-graft, each of the ascending and descending stent-grafts comprising a trunk portion and a reduced diameter portion, the reduced diameter portion coupled to the trunk portion and concentrically offset from the trunk portion.

26. The endoprosthesis of claim 25, wherein the reduced diameter portions of each of the ascending and descending stent-grafts comprises a plurality of alternating first and second stent-rings, wherein the first stent-rings have a first diameter and the second stent-rings have a second diameter different than the first diameter.

27. A method comprising:
precannulating an aortic arch of a patient with two guidewires prior to deploying a descending stent-graft;
deploying the descending stent-graft within a descending portion of the aortic arch;
deploying an ascending stent-graft within an ascending portion of the aortic arch; and
deploying a side-branch stent-graft through a fenestration in one of the ascending stent-graft and the descending stent-graft.

28. A method comprising:
deploying a descending stent-graft within a descending portion of an aortic arch, the descending stent-graft comprising a trunk portion and a reduced diameter portion, the reduced diameter portion concentrically offset from the trunk portion;
deploying an ascending stent-graft within an ascending portion of the aortic arch; and
deploying a side-branch stent-graft through a fenestration in one of the ascending stent-graft and the descending stent-graft.

29. A method comprising:
deploying a descending stent-graft within a descending portion of an aortic arch;

deploying an ascending stent-graft within an ascending portion of the aortic arch, the ascending stent-graft comprising a trunk portion and a reduced diameter portion, the reduced diameter portion concentrically offset from the trunk portion; and deploying a side-branch stent-graft through a fenestration in one of the ascending stent-graft and the descending stent-graft.

\* \* \* \* \*